United States Patent [19]

Trop et al.

[11] 4,148,703
[45] Apr. 10, 1979

[54] METHOD OF ELECTROPHORETIC PURIFICATION OF ENZYMES AND PEPTIDES BY MEANS OF AN ADJUSTABLE, SPECIALIZED, GEOMETRICALLY LOCATED ELECTRODE SYSTEM

[75] Inventors: Moshe Trop; Joseph Herbst, both of Brooklyn, N.Y.

[73] Assignees: Morton Weintraub; Bernard Gendelman, both of Brooklyn, N.Y.

[21] Appl. No.: 657,232

[22] Filed: Feb. 11, 1976

[51] Int. Cl.$^2$ ................... G01N 27/26; G01N 27/30
[52] U.S. Cl. ........................ 204/180 G; 204/180 R; 204/299 R
[58] Field of Search ........... 204/180 R, 180 S, 180 G, 204/299, 300

[56] References Cited

U.S. PATENT DOCUMENTS

| | | | |
|---|---|---|---|
| 2,853,448 | 9/1958 | Heiskell, Jr. | 204/299 |
| 3,255,100 | 6/1966 | Raymond | 204/180 G |
| 3,384,568 | 5/1968 | Kato et al. | 204/299 X |
| 3,567,611 | 3/1971 | Michel et al. | 204/299 |
| 3,616,457 | 10/1971 | Hjerten et al. | 204/299 |
| 3,773,645 | 11/1973 | Nees et al. | 204/299 |
| 3,773,648 | 11/1973 | Van Welzen et al. | 204/299 |
| 3,788,969 | 1/1974 | De Stefano et al. | 204/299 |
| 3,865,712 | 2/1975 | Davies | 204/299 |
| 3,988,230 | 10/1976 | Krotz | 204/180 G |

*Primary Examiner*—Arthur C. Prescott

[57] ABSTRACT

The method of electrophoretic purification of enzymes & peptides which is a continuous, modularized, one-step operation. The method enables the user to secure a high purification of enzymes and peptides simultaneously as it allows their purification on a large scale, the process is modularized with interchangeable parts and contains several divergent configurations such as diagonal linear electrodes, point or ball electrodes, parabolic electrodes, arced electrodes, and other geometrically shaped electrodes. The modularization permits the easy insertion and removal of different geometrically shaped electrodes which allow a multifunctional versatile implementation and application of electrophoresis in the purification of electrically charged biomolecules. The different geometrically shaped electrodes also permit potentially different gradients, thereby enabling different particle velocities, finer separations, and continuous electrophoresis, by means of a higher voltage, in a smaller area, with a decrease in power expenditure. The method includes such innovative features as automatic switching, and repetitive & selective operation of the divergent geometrically shaped electrode systems. The automatic switching consists of electronic circuits which alternately select the various electrode systems to be turned on and off at a given time independently of one another, for a given duration of time, in order to maintain a clearly defined electrical field distribution, or gradient, along the width and length of the gel. The repetitive & selective operation of the divergent geometrically shaped electrode systems enable the selection of the most suitable geometrically shaped electrode system to obtain optimum separation in the purification of particular electrically charged biomolecules.

7 Claims, 16 Drawing Figures

METHOD OF ELECTROPHORETIC PURIFICATION OF ENZYMES AND PEPTIDES BY MEANS OF AN ADJUSTABLE, SPECIALIZED, GEOMETRICALLY LOCATED ELECTRODE SYSTEM

BACKGROUND AND SUMMARY OF THE INVENTION

An improvement in the method of purifying enzymes and peptides that is continuous, one step in operation, and modularized, which utilizes polyacrylamide gel as a medium for continuous separation but does not make use of a flowing of the buffer through the gel. The method is continuous, in that the flow of the stream of crude enzymes and peptides is not interrupted during any stage of the operation. The method is one-step in the operation of purification as the enzymes and peptides, from the time they are fed into the gel, undergo a process of purification which requires no additional steps of purification. The electrophoresis on the polyacrylamide gel results in high purification as the polyacrylamide is one unified piece of gel which purifies higher than any other substance because it provides a high molecular sieving resolution. The "Adjustable Specialized Geometrically Located Electrode System" results in purification of enzymes and peptides on a large scale, for the different geometrically shaped electrodes provide different pathways for each different enzyme and peptide existing in the crudely applied mixture thereby enabling the separation, elution, and collection of typical enzymes and peptides, though as many as one hundred different enzymes and peptides are caused to flow from the crude protein mixture through the gel at the same time. The modularization of the interchangeable parts of the electrode system, which include such geometrically different shapes as diagonal linear electrodes, arced electrodes, parabolic electrodes, point and ball electrodes, and other shapes, create a diversity of field gradients by causing many different particle vectors, and permit a multifunctional versatile implementation and application of electrophoresis in the purification of the enzymes and peptides. The automatic switching system of the electrodes, which last from 1/100th of a second to 10 seconds, and the on and off repetitive selectivity of the electrodes, enable the prevention of the electrode system's interference on one another, and enable the avoidance of short circuits, thereby providing the creation of required potential vectors. The "Adjustable, Specialized, Geometrically Located Electrode System" containing the innovative features of modularization of electrode systems, automatic switching, repetitive and selective operations of the divergent geometrically shaped electrode systems, and the divergent geometrically shaped electrode systems, have not been used in the past or present methods of electrophoresis.

The method allows a high purification simultaneously as it allows purification on a large scale, dual factors which do not exist together under present methods of electrophoresis. The method conceives a separation in a rectangular thin gel placed between the separate independent fields perpendicular to each other. The two electric streams are not operated simultaneously, but rather intermittently, during short periods of time, switched automatically by controlled automatic switches. However the gel itself is under a convertable single electrical field continuously. The intensity of one field or both fields, is in a gradient form alongside the width of the field applied onto the gel layer. This is accomplished by introducing electrodes, forming the respective fields, in such a way that the resistance of the medium is gradually changed along the width of the field. These changes are adjusted to follow many different curves such as linear, exponential, hyperbolic, circular and other shapes, by altering the geometric location and shapes of these electrodes, the theory being that a greater rate of change in the field yields a finer separation of particles. A typical configuration of the linear gradient can be achieved by placing electrodes diagonally alongside the gel and using the variations in diagonal to control the slope of the gradient. The exponential gradient may be achieved in the same manner as the linear but using an exponential curve in the electrodes. The point or ball electrodes in an exponential system consist of electrodes in small circles of buffers, one for positive and one for negative. These electrodes when placed as indicated (in FIG. 2) produce a field which has an exponential effect on the particle accelerations thereby yielding better particle separation. Other variations such as concave and convex hyperbolic curves have proven to yield beneficial results. The enzymatic preparation mixture is introduced into the gel continuously by a very slow constant flow, through a thin tubing into a hole crossing the thickness of the gel, during the application of the electrical fields. The vertical electrical field is the "separator" of proteins according to their mobility in the field on account of the net charge, molecular dimension, and molecular configuration, by applying upon them a vertical vector (A). The horizontal electrical field applies a vector (B) and causes the proteins to move horizontally. The proteins pass through the gel via a series of tiny holes across the thickness of the gel, eluted by the flowing buffer which runs during the operation. The gradient is the factor which enables the faster fractions to emerge sooner and closer to the application point than the slower ones. An ambient temperature is maintained at any degree needed by circulation of coolant around a vertical plate from a refrigerated bath, permitting preparative separations for heat labile substances such as enzymes. A combinational system is used to yield better separation. Each band that is separated is run through higher voltage, an electrode separation having better differentiation to obtain a finer yield. The advantage is that a smaller system is required for a greater batch of input. Another advantage is that less heat is dissipated by the system due to the lower voltage required for a smaller system.

Figures 9, 10, 11:
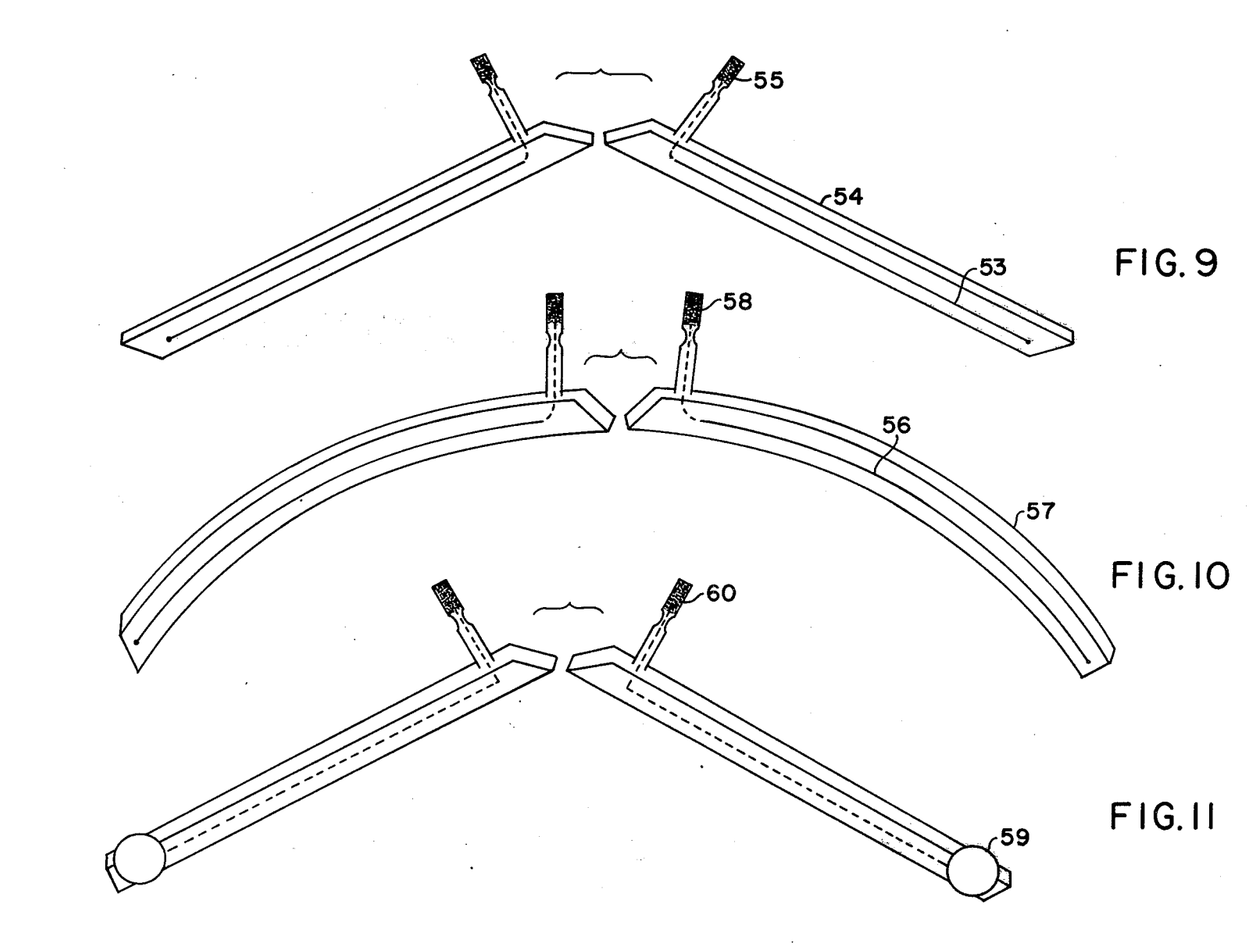
FIGS. 9, 10 and 11 depict electrode nodules.
Figure 12:
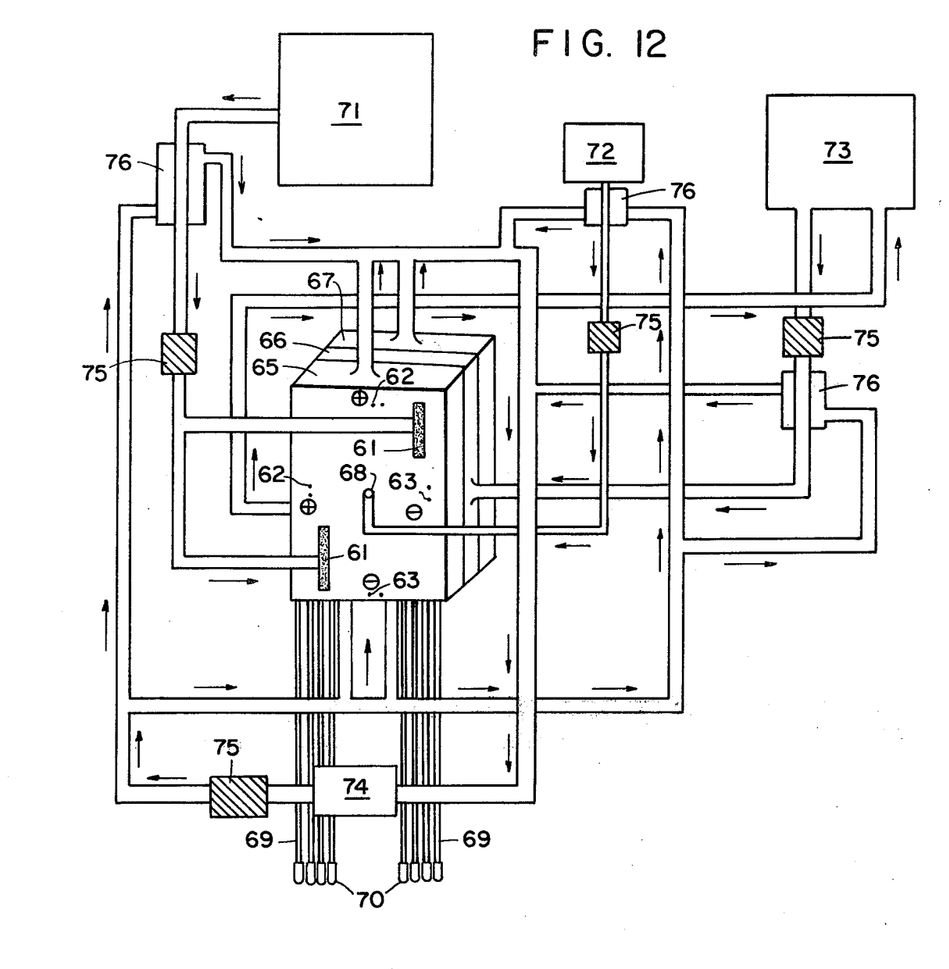
FIG. 12 illustrates a flow system for the process of the invention.

FIG. 12 shows the scheme of the various parts of the electrophoresis apparatus and the different flowing fractions. FIGS. 1, 2, 3 & 4 show the scheme of the separating vectors. FIGS. 9, 10 & 11 shows different kinds of modularized electrodes.

DESCRIPTION OF PRIOR ART

Enzymes and peptides are protein molecules that catalyze and perform chemical reactions on animals, plants, and microorganisms. The enzymes cause the chemical reactions to occur thousands and even millions of times faster than if the enzymes were not present. In the human body alone there are more than a thousand different types of enzymes. Industrial enzymes are derived from plant or animal tissue or from the cells of microorganisms. To obtain these endoenzymes the cells of the enzyme source are removed from its associated liquid which contain the secreted enzyme. When necessary, preservatives are added to these extracts, which are sybsequently clarified. Enzyme syrups or powdered preparations are made from these solutions which are concentrated but not highly purified. The production of high purity enzymes require alternative steps, successive and/or independent, which start with the raw material or protein mixture. These steps include: fractional precipitation; differential adsorption and elution; chromotography; electrophoresis; dialysis; crystalization; and freeze drying.

Electrophoresis is widely used as a separation technique, particularly in protein chemistry. It has been valuable as a "gentle" analytical method for complex organic material enzymes, hormones, proteins, collagens, amino acids, nucleotides etc. that are changed and destroyed by heat or chemical action. Many kinds of electrophoretic apparatuses have been developed in order to achieve convenient, inexpensive, and relatively rapid methods of purifying large quantities of proteins or providing a high purification. However, there is no electrophoretic method at present that utilizes an application of purifying enzymes and peptides which perform both of these results together and simultaneously-to yield a higher purification and to provide purification on a large scale. Nevertheless, physicochemical and structural studies of proteins demand that the protein be extremely high in purity and require rather large quantities of the purified protein.

Since 1808, when Reuss first discovered the potentialities of the method of electrophoresis by observing the transfer of water from an anode chamber to the cathode chamber as an electric current passed through an earthenware diaphragm, and 1880, when Kohlrausch, Henry and others developed the electrokinetic theory, and 1930, when Tiselus developed the moving boundary method, the improvements in the electrophoretic process has been vast and worthy indeed. At the present time there are at least 18 different classifications of electrophoretic methods based upon medium types, and approximately 100 more or less different techniques within these classifications, however, each one of these classifications have not altered or modified the standard application of one pair of parallel electrodes in an equal field. Each one of these classifications do not provide the simultaneous results of both high purification of enzymes and peptides and purification of the same on a large scale. A review of all the present classifications of electrophoretic processes include the following medium types all of which do not contain the innovative features of our invention which consist of modularization of electrode systems, automatic switching, divergent geometrically shaped electrode systems, and repetitive & selective operations of the said systems.

The 18 different classifications include the following:

1. The Microscopic (analytical) medium type which is a free supporting medium, contains one pair of parallel electrodes in an equal field. (See reference #1).
2. The Boundary (analytical) medium type which includes a free supporting medium (see reference #2) or which includes a supporting medium where no molecular sieving is performed (see reference #3) contain one pair of parallel electrodes in an equal field.
3. The Zone Electrophoresis (analytical) medium type which includes a supporting medium of no molecular sieving (see reference #4) or which includes a supportive medium of molecular sieving (see reference #5) contain only one pair of parallel electrodes in an equal field.
4. The Zone Electrophoresis Preparative (two-stage) medium type, which includes a free supporting medium (see references #6 & #7), or which includes a supporting medium of no molecular sieving (see reference #8) or which includes a supportive medium of molecular sieving (see reference #9) contain only one pair of parallel electrodes in an equal field.
5. The Zone Electrophoresis Preparative (single-stage (a) flow elution) medium type, which includes a supporting medium of no molecular sieving (see reference #10) or which include a supporting medium of molecular sieving (see reference #13) contain only one pair of parallel electrodes in an equal field.
6. The Zone Electrophoresis Preparative (continuous) medium type which includes a supporting medium (see reference #14 & #15) or which includes a supportive medium of no molecular sieving (see references #16 & #17) or which includes a supportive medium of molecular sieving (see reference #18) contain only one pair of parallel electrodes in an equal field.

All these 18 different classifications of medium types, include approximately, more or less, 100 different known techniques and approaches, all of which do not make use of the innovative features of our invention which consist of modularization of electrode systems, automatic switching, divergent geometrically shaped electrodes, and the repetitive and selective operations of the said systems.

SUMMARY OF THE INVENTION

It is therefore among the principal objectives of this invention to improve on the method of electrophoresis by satisfying two conditions simultaneously, the high purification of enzymes and peptides and the purification of enzymes and peptides on a large scale, without the usual concomitant disadvantages of non-electrophoretic purifying techniques, requiring increased procedural steps, increased time, increased labor, & increased costs. The improvement contemplates and includes within its scope a continous preparative electrophoresis in which polyacrylamide gel serves a medium for continuous separation but without a flowing of the buffer through the gel. The new method conceives a separation in a rectangular thin layer gel placed between two separate independent field systems perpendicular to each other. The two electrical field systems do not function simultaneously, but rather operate during short periods of time and are switched automatically by controlled automatic switches. The gel itself is continuously under a convertable single electrical field. The intensity of both fields is adjustable by its geometric shape and makes a gradient form alongside the width of the field applied onto the gel layer. This is accomplished by the introduction of both electrodes in a diagonal position in such a way that the resistance of the medium is gradually decreased along the width of the field. The apparatus and temperature is regulated by achieving fractionation of heat sensitive materials. The enzymatic preparation mixture is introduced into the gel continuously by a very slow constant flow through a thin tubing into a hole crossing the thickness of the gel during the application of the electrical fields. The vertical field "separates" the proteins according to their mobility in the field, on account of the net electric charge, the molecular dimension, and the molecular construction, by applying on them a vertical vector (A). The horizontal electrical field applies a horizontal vector (B) and causes the proteins to move horizontally. The proteins pass through the gel and out via a series of tiny holes across the thickness of the gel, eluted by the flowing buffer which runs during the operation. The gradient factor enables the faster fractions to emerge sooner and closer to the application point than the slower ones. An ambient temperature is maintained at the needed degrees by the circulation coolant around a vertical plate, from a refrigerated bath, permitting preparative separation for heat labile substances sych as enzymes. The modularized interchangeable parts contain several diverse configuration including diagonal linear electrodes, exponential electrodes, arced shaped electrodes, and other geometrically shaped electrodes. These different geometric shapes apply different particle velocities, thereby enabling a finer separation, & a continuous electrophoresis, by means of higher voltage in a smaller area with less expenditure of power. These different geometric shapes allow a high purification of enzymes and peptides simultaneously, as the continuous electrophoresis permits purification of enzymes and peptides on a large scale.

While for the ease of convenience the specification will refer throughout the application to the following structures:

A. Chassis Main Body (FIG. 13; 7) which includes a rectangular structure containing gel that has input ports for crude preparation and output ports for the enzyme output, interconnection brackets for the connection of accelerating and separating electrodes, and electrode systems. On the left side, where the positive particles gravitate, is located the positive separating electrode system which separates only positive electrodes, positive separating electrodes positive, and positive separating electrodes negative. On the right side, where the negative particles gravitate, is located the negative separating electrode system which separates only negative electrodes, negative separating electrodes negative, and negative separating electrodes positive.

B. Chassis Sub Body which include the electrodes that are hooked up to the sides:

1. (77) Cross accelerating electrodes, positive and negative ones.

2. Separating electrodes which go along side the length of the chassis body, both for positive enzymes and negative enzymes.

(a) (78) Negative separating electrodes, both positive and negative.

(b) (79) Positive separating electrodes, both negative and positive.

These are situated alongside the periphery of the chassis.

C. Accessories of the System which include those systems that aid indirectly the separation process performed by the chassis main body and the chassis sub body.

1(81) Feeding system—which contains a pump, tubing, and an interconnecting reservoir to the gel.

2. Output buffer system—which contains a pump, reservoir of buffer.

3. Cooling system—which contains a pump, refrigerant reservoir, circulating wrapped coils of water or a refrigerant.

4. (85) Electronic switching network—which contains positive and negative accelerating electrodes, positive and negative separating electrodes, and positive and negative separating electrodes.

Figure 14:
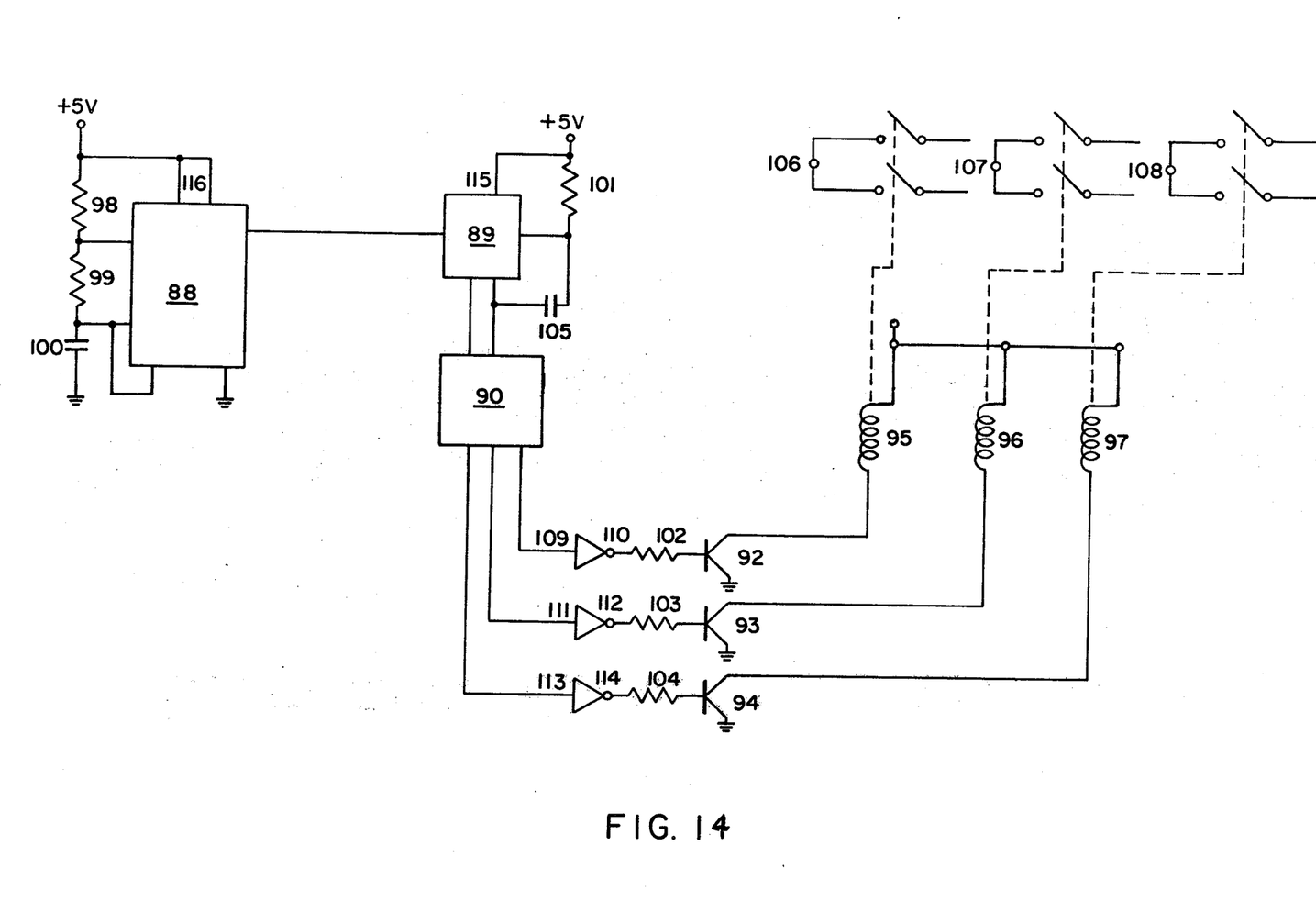
FIGS. 14 and 15 illustrate the electronic switching network.
Figure 15:
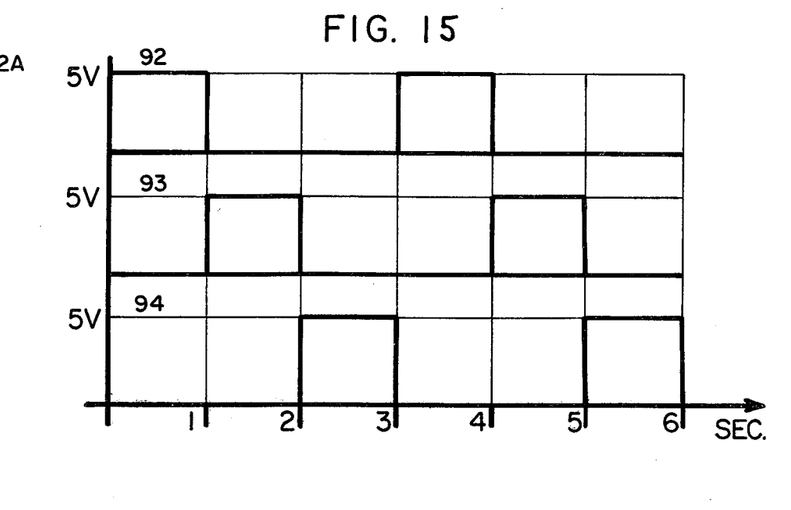

In FIGS. 14 & 15 a. Timer—which determines the time interval of switching from one system to the next.

In FIGS. 14 & 15 b. Counter—which counts the pulses from the timer to distinguish each count, thereby defining the status, acceleration, positive separation and negative separation.

In FIGS. 14 & 15 c. Decoder—which differentiates the states from the counter, decodes the states of the counter, and receives the counter's, output which is binary and decodes it to individual outputs.

The specification includes the following dimensions, time intervals, and ranges:

Length of gel—range from 3.5 centimeters to 30 centimeters.

Width of gel—range from 2 centimeters to 20 centimeters.

Current: 250 to 1000 volts.

Feeding rate—from 15 to 50 miligrams an hour of crude protein.

High purification—one bent Drawings consist of the following: FIGS. 1, 2, 3 & 4 illustrate the principle of the separation of enzymes and peptides by a combination of two perpendicular lines.

Figures 1, 2:
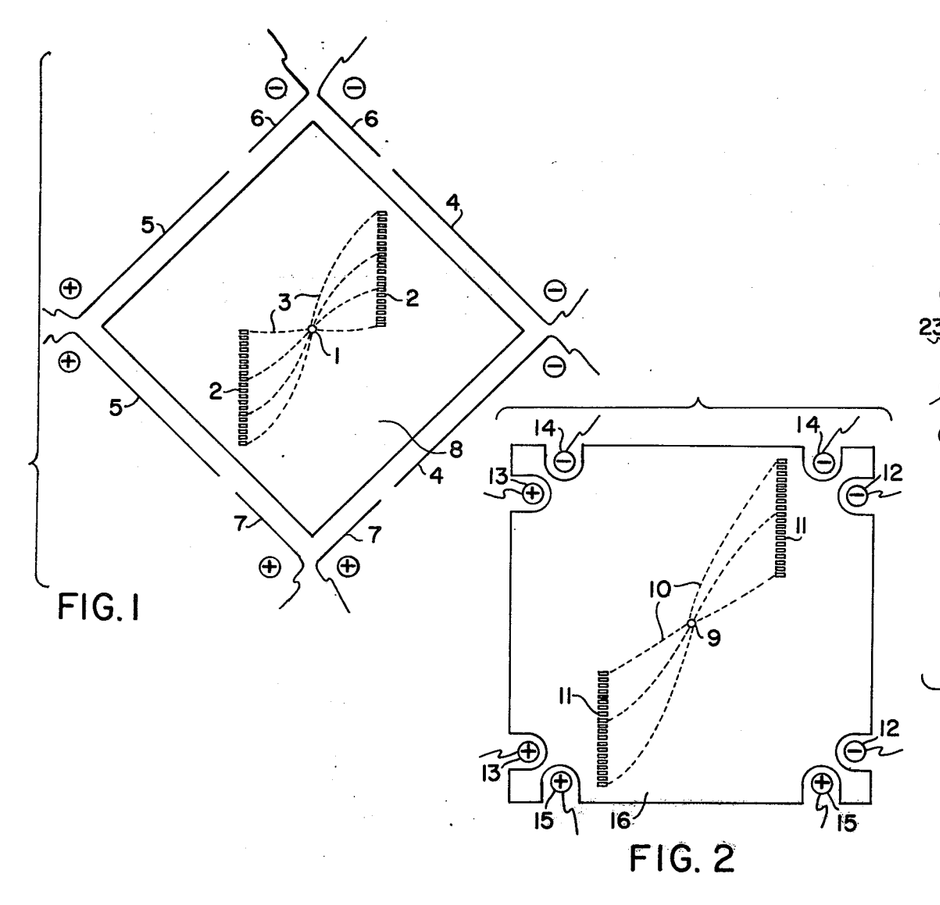
FIG. 1 represents a view of the cell using diagonal linear electrodes.
FIG. 2 shows a view of the cell with ball electrodes.

In FIG. 1: 1—represents the inlet hole; 2—the outlet holes; 3—the line movements of enzyme or peptide fractions; 4—horizontal separating negative electrodes; 5—horizontal separating positive electrodes; 6—vertical accelerating negative electrodes; 7—vertical accelerating positive electrodes. FIG. 1 depicts the diagonal linear electrodes.

In FIG. 2:9—represents the inlet hole; 11—the outlet holes; 10—the line movements of enzyme or peptide fractions; 12—horizontal separating negative electrodes; 13—horizontal separating positive electrodes; 14—vertical accelerating negative electrodes; 15—vertical accelerating positive electrodes; 16—the gel. FIG. 2 depicts the ball electrodes.

Figure 3:
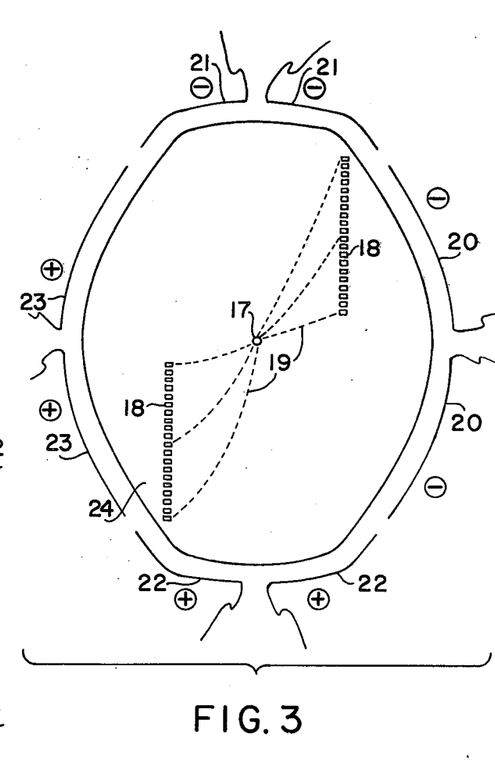
FIG. 3 depicts the cell with parabolic electrodes.

In FIG. 3:17—represents the inlet hole; 18—represents the outlet holes; 19—the line movements of enzyme or peptide fractions; 20—horizontal separating negative electrodes; 23—horizontal separating positive electrodes; 21—vertical accelerating negative electrodes; 22—vertical accelerating positive electrodes; 24—the gel. FIG. 3 depicts the parabolic electrodes.

Figure 4:
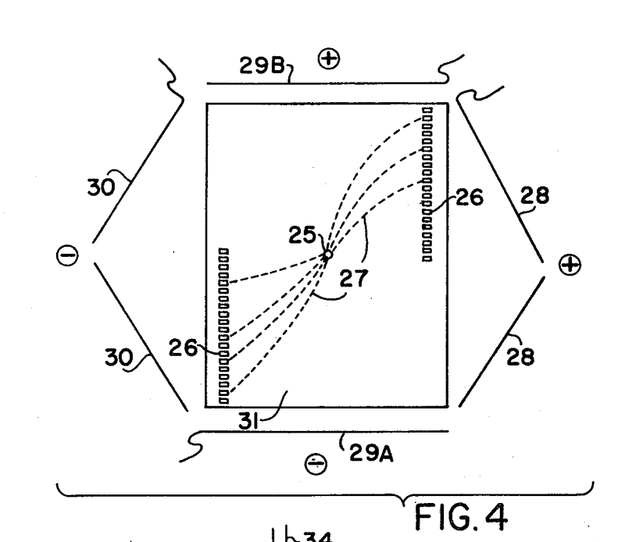
FIG. 4 depicts the cell with parallel linear electrodes.

In FIG. 4:25—represents the inlet hole; 26—the outlet holes; 27—the line movements of enzyme or peptide fractions; 30—horizontal separating negative electrodes; 28—horizontal separating positive electrodes; 29A—vertical accelerating negative electrodes; 29B—vertical accelerating positive electrodes; 31—the gel. FIG. 4 depicts the parallel linear electrodes.

FIGS. 5, 6, 7 & 8 illustrate the three chambers combined to form an electrophoresis cell.

Figure 5:
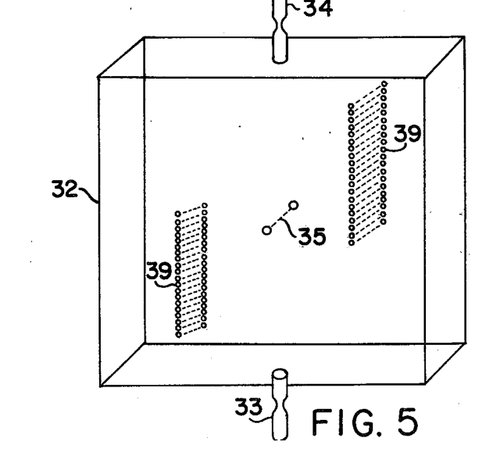
FIGS. 5, 6, 7 and 8 illustrate the three chambers combined to form an electrophoresis cell.

In FIG. 5:32—represents chamber #1; 33—inlet mouthpiece of circulating water coolant; 34—outlet mouthpiece of circulating water coolant; 35—outlet mouthpiece and central channel hole which provides passage for the crude extract preparation waste. 39—the comb-like holes which receives the elution buffer.

Figure 6:
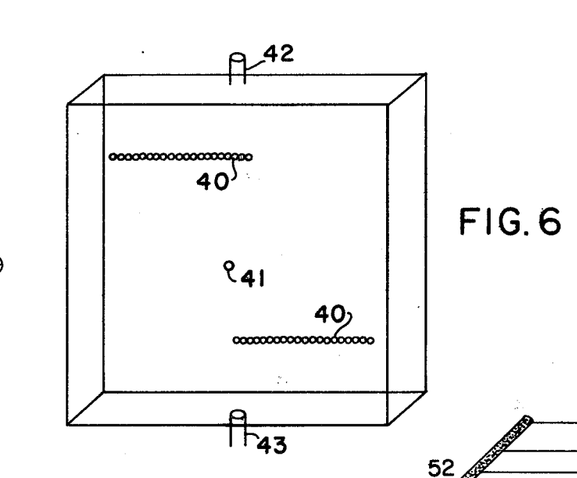

FIG. 6 represents chamber #2; 40—the comb-like holes which receive the elution buffer; 41—outlet central channel hole which provides passage for the crude extract preparation waste; 42—inlet mouthpiece for electrode buffer circulation; 43—outlet mouthpiece for electrode buffer circulation.

Figure 7:
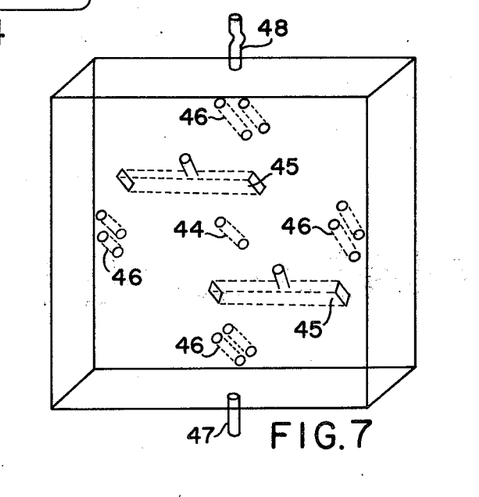

FIG. 7 represents chamber #3; 44—inlet mouthpiece for crude extract penetration; 45—inlet chamber and mouthpiece for passage of eluting buffer into electrophoretic unit; 46—inlet holes for electrodes; 47—inlet mouthpiece of circulating water coolant; 48—outlet mouthpiece of circulating water coolant.

Figure 8:
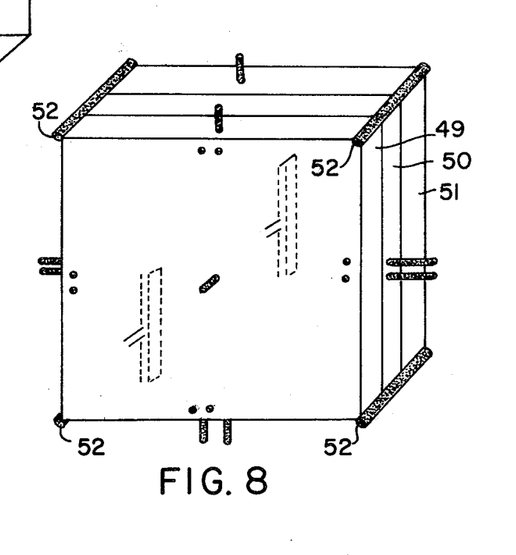

FIG. 8 represents the 3 chambers combined; 49—chamber #3; 50—chamber #2; 51—chamber #1; 52—chamber joiner screws.

FIGS. 9, 10 & 11 illustrates the electrode modules.

FIG. 9: 51—platinum wire; 54—plastic sheath; 55—plug. FIG. 9 depicts the diagonal linear electrode module.

FIG. 10: 56—platinum wire; 57—plastic sheath; 58—plug. FIG. 10 depicts the diagonal linear electrode module.

FIG. 10 depicts the parabolic electrode module.

FIG. 11: 59—ball coated with platinum; 60—plug. FIG. 11 depicts the ball electrode module.

FIG. 12 illustrates the fluids flow system. 61—inlet hole chamber of the eluting buffer; 62—anode inlet; 63—cathode inlet, combined electrophoretic chambers; 65—chamber #3; 66—chamber #2; 67—chamber #1; 68—inlet of the crude extract preparation into the cell; 69—fraction hoses, passage of fractions following separation; 70—fraction collector tubes or bottles; 71—eluting buffer reservoir; 72—crude extract preparation reservoir 73—electrode buffer reservoir; 74—cooling system unit; 75—pump, for driving liquid; 76—cooling water sleeve.

Figure 13:
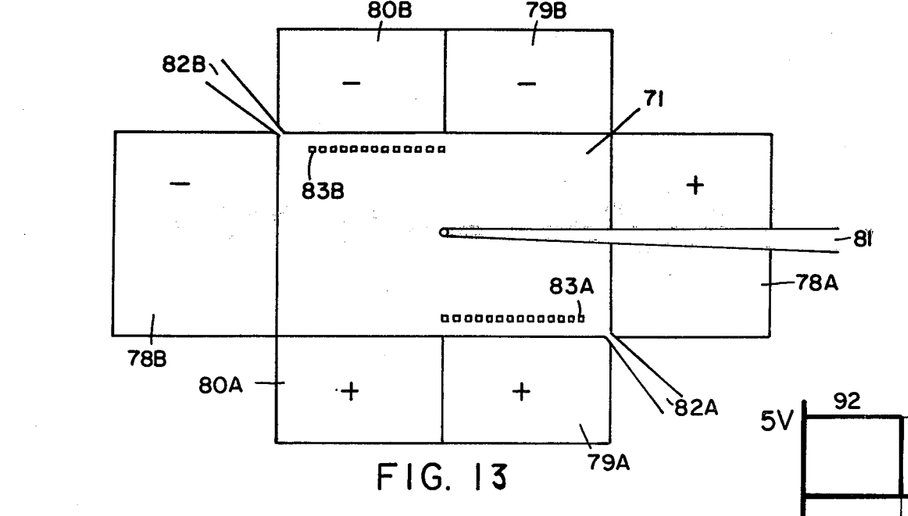
FIG. 13 is a block drawing of the nodularized classes and subclasses.

FIG. 13: Block drawing of modularized chassis and subchassis: 77—main chassis body; 78A—cross accelerating electrode module positive; 78B—cross accelerating electrode module negative; 79A—negative separating electrode module, positive; 79B—negative separating electrode module, negative; 80—positive separating electrode module, positive; 80—positive separating electrode module, negative; 81—input feed system, crude extract preparation; 82A—to output buffer system; 82B—to output buffer system; 83A—comb-like holes, output; 83B—comb-like holes output;—cooling system;—electronic switching network;—power supply;and—electrode buffer pumping system network are part of the system but not shown in this Figure.

FIGS. 14 & 15 illustrate the electronic switching network; 88—represents a NE555 timer; 89—74163 binary counter; 90—74154 decoder; 91—7405 hex inverter; 92, 93, 94—2N2222A NPN transistors; 95, 96, 97—high voltage relays; 98, 99, 100 are adjusted to obtain a frequency of 1 beat per second; 101—1K resistor; 102, 103, 104—1K resistor; 105—0.001 ufd capacitor; 106—accelerating power supply; 107—positive separating power supply; 108—negative separating power supply.

Figure 16:
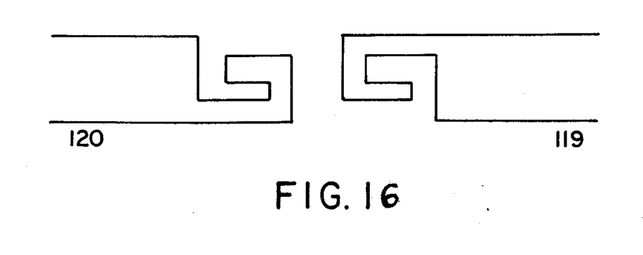
FIG. 16 is a drawing depicting the connection system of the main classes and the electrode nodule.

FIG. 16 is a drawing depicting the connection system of the main chassis and the electrode module. 119—main chassis; 120—electrode module.

Describing now the application of the "Adjustable Specialized, Geometrically Located Electrode System".

1. Three chambers, forming the chassis main body, will be assembled individually, to be subsequently attached in bayonet fahion, whereby the plugs of the electrode system modules are bayonetted into the chambers, which are arranged like a sandwich, wherein chamber #3 and chamber #1 are the outer layers and chamber #2 is the inner layer, wherein chamber #3 the top layer, contains circulating water coolant sheathed in plastic, chamber #2 contains a batch of polyacrylamide gel, electrodes and buffer, and chamber #1, the bottom layer contains circulating water coolant sheathed in plastic.

2. A batch of gel is prepared for the entire system consisting of the chassis main body and the modularized electrodes. The gel is placed in chamber #2, filling it out, between the casing of the chassis main body and cut away with a cutout to a predetermined form corresponding to the geometric shape of the specialized geometric electrode module, selected from a repertoire of different specialized geometric shaped electrode modules, such as a diagonal linear shaped electrode module, a point and ball shaped electrode module, a parabolic shaped electrode module, an arced shaped electrode module and other geometrically chaped electrode modules, to purify specifically enzyme or peptide "X". The gel shape that has been cut away is limited and proscribed by the geometric shape of the electrode module. The superfluous gel, that portion of the gel which extends beyond the boundaries of the geometric shape of the electrode module, is detached and removed from the chassis.

3. Appropriate size channel hole is cut out of the center of the gel of chamber #2 corresponding to the size and location of the prearranged hole in chamber #1 and chamber #3. Through the central channel hole in chamber #3, down through the central channel hole in chamber #2, and down through the central channel hole in chamber #1, each channel hole directly below the channel hole above it, flows the crude extract preparation of enxymes, peptides and other biomolecules.

4. Appropriate size comb-like holes, similar to holes formed by the teeth of a comb on a batch of gel, will be cut out of the gel in chamber #2, which said holes will form two straight parallel lines, one line of holes situated higher than the other line of holes, by about 2 centimeters, each line containing from 10 to 20 evenly spaced comb-like holes, which correspond in size and location to the comb-like holes found in chamber #1. These comb-like holes found in chamber #2 and chamber #1 will subsequently receive elution buffer, which said buffer will flow through the hollow in chamber #3.

5. The separating electrodes and the accelerating electrodes, platinum wires coiled or elongated alongside plastic, are connected to electrode switching circuit which in turn will be connected to the power supply. The automatic switching network will be set to operate, theoretically, 24 hours a day, thereby providing a continuous separation. The chamber #2 is filled up over its entire area with electrode buffer.

6. The mounting screws are tightened both to hold the electrode modules in place and to join all the chambers together to form the complete chassis main body.

7. The electrode buffer circulation system is connected in the appropriate holes in chamber #3 so that the electrode buffer will circulate from a hole in chamber #3, on the extreme left side of the chamber, down to chamber #2, through the area of chamber #2, and up through a hole in chamber #3, at the extreme right side of chamber #3. The electrode buffer system circulates by means of a pump and hoses, the pump pumping the circulating buffer from the starting point the reservoir, via hoses, through chamber #2 and recirculating the buffer via hoses, to the reservoir, located in a special unit.

8. The cooling system of circulating water, circulates via hoses through chamber #3 and passes on downward all the way via hoses leading outward, which said hoses connected to the outlets of the holes found on the bottom of chamber #1.

9. The crude extract preparation of enzymes, peptides, and other biomolecules, is fed through the central channel hole inlet, in chamber #3, by means of a pump, via a hose which passes down from the mouthpiece inlet in chamber #3 down through the central channel in chamber #3, down through the central channel in chamber #2, and down through the central channel in chamber #1, out through the mouthpiece outlet, which said mouthpiece is attached to a hose which leads the residue of the crude extract preparation to a unit collecting waste. The end product, the purified enzyme or peptide, will be collected by fraction collecting tubes, which said tubes are connected to the mouthpieces of the small hoses extending down from the bottom of chamber #1.

10. The circulating electrode buffer system will be connected, the cooling system of circulating water will be connected, the crude extract preparation of enzymes and peptides and other biomolecules will be fed through the connected hoses, through the central channel inlet. The elution buffer will be pumped. The circulating water coolant, however, will be pumped ½ hour prior to the purification process. The electrode switching circuit will be set in motion.

11. The system is now ready to be used for the continuous, one step operation, purification process of enzyme or peptide "X".

12. Every 4 to 5 hours the system's operation will be supervised to monitor the temperature level.

13. At the close of the system's operation the specialized geometric shaped electrode system module, most suitable for the purifcation of enzyme or peptide "X" will be disconnected and removed from the chassis main body, and in its place another specialized different geometric shaped electrode system module most suitable for the purification of enzyme or peptide "Y" will be inserted in the chassis main body. The whole procedure will start anew from 1 through 13.

Describing now the adjustability of the "Adjustable, Specialized, Geometrically Located Electrode System".

The "Adjustable, Specialized, Geometrically Located Electrode System" may be adjusted and adapted to include the modularization of a complete chassis sub body, and a complete chassis main body, not just the electrode system module alone. Describing now the preparation of the adjusted and adapted system and the said system's assembly.

1. A batch of gel is prepared for the entire system consisting of chassis main body and the modularized electrdoes. The gel is placed between the casing of the chassis main body and the output portholes are formed. The gel is also placed between the casing of the modularized electrodes. The shape of each electrode is cut to a predetermined form, depending upon the electrode of the particular module.

2. The platinum electrodes are placed into the cutout and attached to the electrical connection. After this is done the system is ready to be used.

3. The system is now ready to be assembled to be used for a specific purpose which predetermines the type of the electrodes to be used.

4. The chassis main body, the input pump, the output pump, and the output portholes are attached.

5. The accelerating electrodes are attached to the front and back of the chassis main body, and the electrode buffer system is attached to them.

6. The mounting screws are tightened both to hold the electrodes in place and to obtain a better mingling of the electrode gel with that of the chassis main body.

7. The separating electrodes, of the chassis sub body, are then selected (depending on the predetermined data) and mounted alongside the chassis main body similar in manner as the accelerating electrodes.

8. The power supply is then connected to the electrode switching circuit which is then connected to the electrodes and the turn on switch.

Describing now the action of the invention: See FIG. 13:

Article 81, the input feed system, which is a pumping mechanism, pumps the initial mixture into the separating system. Article 77, which is the chassis main body system, contains the gel, the input porthole and the output portholes 83A and 83B. The mixture is then accelerated via positive electrode 78A, and negative electrode 78B. During the cross acceleration the particles are separated to the sides toward the portholes by 79A and 79B, for positive particles which are the positive separating electrodes or negative particles by 80A and 80B which are the negative separating electrodes. All the electrodes are controlled by an electronic switching network so that no two electrode systems are operating simultaneously. Eventually the particles gravitate and collect at the output portholes 83A and 83B, its path being a function of the electrical field, and are forced out via the output buffer pumping system 82A and 82B. The temperature of the system is maintained by a cooling system network, consisting of a pump and coolant. The power supplies, provide power to the electrodes as needed.

Describing now the electronic switching method. The osciltator beats at a frequency of approximately one beat per second and feeds into the counter. The first count is decoded by the decoder which turns on the accelerating electrode switches via the driver. The next beat of the osciltator advances the counter whose output is decoded and turns on the positive separating electrodes, via driver and switches. The next beat resets the counter and the entire cycles starts all over again.

REFERENCES

1. Ellis, G. (1912) Z. Phys. Chem. 78 321
2. Tiselius, A. (1937), Trans. Faraday Soc. 33 524
3. Lodge O. (1886), Report of British Assoc. for the Advancement of Science Birmingham P.389

4. Hjerter S. Jersedt and A. Tiselius (1969), Annal Biochemistry 27 108
5. Smith I. (1968), "Chromotography and Electrophoretic Techniques" Vol.2, "Zone Electrophoresis" Whey. New York
6. Zweig G. and Whitaker J. P., "Paper Chromotography and Electrophoresis" Vol. 1, "Electrophoresis in Stabilizing Media" Acad. Press N.Y.,1967
7. Durrum E. I. (1950), Aemr. Chem. Soc. 72 2943
8. Smithies, O. (1955) Nature 175 309
9. Raymond S. and Weintraub L. (1959), Science 130 711
10. Svenson H. (1948), Advan. Protein Chem. 4 251
11. Svenson H. and Walmet E. (1955), Sci. Tools 2 11
12. Kunkel H. G. and Slater E. (1952), Proc. Soc. Exp. Biol. Med. 80 42
13. Rayomnd S. (1964), Science 146 406
14. Porath J. Lindner E. B. and Jerstedt S. (1958), 182 741
15. Murray K. (1962), Anal. Biochem. 3 415
16. Jovin T., Chrambach A., and Naughton M. A. (1964), Anal. Biochem. 21 190
17. Schenkin I., Levy M., and Weis P. (1968), Anal. Biochem. 25 387
18. Boyde T. R. C. (1971), Occasional Paper #7 from the Dept. of Biochem. Makerere Univ. Kampala
19. Philipot J. Sr. L. (1940), Trans. Faraday Soc. 36
20. Barrollier J., Watzke E. and Cibian I. (1958), Z. Naturforsh 13 b. 754
21. Grossmann W. and Hannig K. (1949), German Pat. #805,344
22. Boyde T. R. C. and Remtulla M. A. (1973) Anal. Biochem. 55 492

What is claimed:

1. An improvement in the method of electrophoretic purification of enzymes and peptides on a polyacrylamide gel, wherein the improvement includes the adaptation of geometrically located electrode systems situated both in a vertical electrical field and in a horizontal electrical field, which said improvement enables a high purification simultaneously as it allows purification on a large scale, which said improved method having steps comprising:
   Situating divergent geometrically located and divergent geometrically shaped electrode systems in two separate electrical fields, which said electrical fields comprise a vertical electrical field and a horizontal electrical field;
   operating said electrical fields intermittently during selective repetitive periods of time;
   applying a vertical vector, by means of the vertical electrical field systems, to separate the enzymes and peptides in accordance with their mobility; and,
   applying a horizontal vector, by means of the horizontal electrical field systems, to cause the enzymes and peptides to move horizontally.

2. An improved method as recited in claim 1 comprising the further step of alternately selecting the various electrode systems by means of automatic switching, which said automatic switching turns on and off said electrode systems independently of one another for a given period of time and which said automatic switching maintains a clearly defined electrical field distribution and gradient along the width of the gel.

3. An improvement in the method of electrophoretic purification of enzymes and peptides on a polyacrylamide gel, wherein the improvement includes the selective application of divergent geometrically shaped electrode systems, which said divergent geometrically shaped electrodes enable a high purification continuously on a large scale, which said improved method having steps comprising:
   Applying different particle velocities by means of divergent geometrically shaped electrode systems; and,
   enabling a finer separation and a continuous separation of said enzymes and peptides by means of an increased voltage in a decreased area.

4. An improved method as recited in claim 3 comprising the further step of inserting or removing divergent geometrically shaped electrode systems by means of diverse modularized interchangeable units of divergent geometrically shaped electrodes which said interchangeable units having interconnection bracket means to hook onto the side of the rectangular gel structure.

5. The purification method using divergent geometrically shaped electrode systems, as recited in claim 3, which said electrode systems comprising concave and convex electrode systems.

6. The purification method using divergent geometrically shaped electrode systems as recited in claim 3, which said electrode systems comprising point and ball electrode systems.

7. The purification method using divergent geometrically shaped electrode systems as recited in claim 3, which said electrode systems comprising U shaped, inverted U shaped, V shaped and inverted V shaped electrode systems.

* * * * *